United States Patent [19]
Cesa et al.

[11] Patent Number: 4,749,811
[45] Date of Patent: Jun. 7, 1988

[54] METHOD OF MAKING A DIASTEREOMERIC MIXTURE CONTAINING TWO DIASTEREOMERIC α-ACYLOXY ACID ESTERS

[75] Inventors: Mark C. Cesa, South Euclid; Robert A. Dubbert, Solon; James D. Burrington, Richmond Heights, all of Ohio

[73] Assignee: The Standard Oil Company, Cleveland, Ohio

[21] Appl. No.: 792,420

[22] Filed: Oct. 29, 1985

[51] Int. Cl.$^4$ .................... C07C 59/08; C07C 69/66
[52] U.S. Cl. .................................. 562/589; 560/185; 562/579
[58] Field of Search ................ 562/579, 589; 560/185

[56] References Cited

U.S. PATENT DOCUMENTS 2,388,688 11/1945 Hass .................................... 560/185
4,377,708 3/1983 Morris ................................ 582/589

OTHER PUBLICATIONS

Bittler, K. et al., *Angew. Chem.*, vol. 80 (1968) pp. 352–359.
Kitamura, Takanori et al., Chemical Abstracts, vol. 98 (1983) #106,821g.

*Primary Examiner*—Paul J. Killos
*Attorney, Agent, or Firm*—C. S. Lynch; D. J. Untener; L. W. Evans

[57] ABSTRACT

In the process of hydrocarboxylating an enol acylate with CO and an organic hydroxyl compound to produce an α-acyloxy acid ester, the improvement comprising using as the organic hydroxyl compound reactant, an organic hydroxyl compound which has a chiral center that is essentially all L or D, thereby producing a reaction mixture having essentially no enantiomeric pairs and containing diastereomeric α-acyloxy acid esters having two chiral centers.

2 Claims, No Drawings

METHOD OF MAKING A DIASTEREOMERIC MIXTURE CONTAINING TWO DIASTEREOMERIC α-ACYLOXY ACID ESTERS

This invention relates to a process for making an optically active mixture of an α-acyloxy acid ester containing at least two chiral centers.

The separation of enantiomers by physical means such as fractional distillation or fractional crystallization and the like is known to be highly difficult in general.

It is an object of the invention to provide a process to produce a reaction mixture containing α-acyloxy acid esters having two (at least) chiral centers, which mixture contains two of four possible optical configurations and contains substantially no enantiomeric pairs.

Other objects, as well as features, aspects, and advantages, of the invention will become apparent from a study of the specification, including the examples and the claims.

We have now conceived a process for making such a mixture.

Thus, in accordance with the present invention we have provided a process for making a separable reaction mixture containing diastereomeric α-acyloxy acid esters having at least two chiral centers, which process comprises hydrocarboxylating an enol acylate with carbon monoxide and an organic hydroxyl compound having a chiral carbon atom, said organic hydroxyl compound being essentially only in either the L configuration or the D configuration, to produce a reaction mixture of diastereomeric α-acyloxy acid esters having two chiral centers, which mixture contains essentially no enantiomeric pairs.

Further in accordance with the present invention, there is provided a process which comprises hydrocarboxylating an enol acylate according to the equation:

$$R_1R_2C=C(R_3)OCOR_4 + CO + R_5OH \rightarrow R_1R_2CHC(R_3)(OCOR_4)COOR_5$$

to produce an essentially diastereomeric mixture of two α-acyloxy acid esters having at least two chiral carbons, wherein (A) the carbon bonded to $R_3$ in the product is chiral, (B) $R_3$ is not the same as $-CHR_1R_2$, $-COOR_5$, or $-OCOR_4$, (C) each of $R_1$, $R_2$, $R_3$, $R_4$, and $R_5$ contains no ethylenic or acetylenic unsaturation, (D) each of $R_1$, $R_2$, $R_3$, and $R_4$ is independently selected from H and a hydrocarbyl group having 1-15 carbon atoms, and $R_5$ is a hydrocarbyl group having 1-15 carbon atoms, which optionally contains one or more hydroxyl groups, (E) $R_1$ and $R_2$, $R_1$ and $R_3$, or $R_2$ and $R_3$ can be linked to form a ring, and (F) $R_5$ contains a chiral carbon atom which is essentially all L or all D.

When the organic hydroxyl compound reactant is essentially all L, the reaction product mixture contains the diastereomeric α-acyloxy acid esters of the configurations DL and LL, wehre the first designation is the configuration at the alpha carbon atom and the second is the configuration of the chiral center in $R_5$. If the starting material $R_5OH$ is essentially all D optical isomer, the diastereomeric reaction product mixture contains the diastereomeric α-acyloxy acid esters of the configurations DD and LD.

Specific examples of optically pure organic hydroxyl compound reactants useful in the present process include D- or L-3-methoxy-1 butanol, D- or L-2-octanol, L-methanol, D- or L-2-butanol and L-menthoxyethanol.

In most instances each of $R_1$, $R_2$, $R_3$ and $R_4$ is independently selected from H or hydrocarbyl having 1-10 carbon atoms.

The process of the invention for making the mixture containing two (or more) diastereomeric α-acyloxy acid esters is of importance in providing a source for relatively easily obtaining a particular stereoisomeric configuration of a given α-hydroxy acid separated from any other stereoisomer thereof. The mixture made according to the present invention can be resolved by ordinary measures. Thus, the two diastereomers can be separated by well known physical means, such as fractional crystallization, fractional absorption on solid absorbents, countercurrent solvent extraction, fractional distillation where feasible, or other physical means. For a discussion see, for instance, J. Jacques, A. Collet an S. H. Wiler, *Enantiomers, Racemates, and Resolutions*, New York, 1981, Chapters 5 and 7. Thereafter, the product fractions are separately hydrolyzed in the presence of an acid or base in the conventional manner to obtain the corresponding α-hydroxy acids and the chiral, optically active (L or D) organic hydroxyl compound. This is especially useful because it allows an overall process involving recycle of the chiral alcohol. Thus, in this aspect of the invention, the organic hydroxyl compound which is regenerated during the hydrolysis is recycled at least in part to the step of hydrocarboxylating, thus allowing repeated use of the organic hydroxyl compound.

The present invention is of considerable value in providing a route for making of the L form or the D form α-hydroxy acids occurring in nature. In this aspect of the invention the product is a diastereomeric mixture containing α-acyloxy acid esters that are hydrolyzable to naturally occurring α-hydroxy acids. The present invention is of considerable advantage when compared to present methods. Thus, optically pure α-hydroxy acids are produced industrially by the following methods:

(a) fermentation
(b) chemical synthesis using HCN as a one-carbon source, follwed by derivatization and resolution and subsequent de-derivatization.

Fermentation processes, while they give highly enantiomerically pure product, are costly and insufficient in that they produce large amounts of by-products, making product purification expensive and troublesome. The chemical routes are highly corrosive, consume stoichiometric amounts of toxic and expensive HCN and $H_2SO_4$, produce stoichiometric amounts of low-value ammonium sulfate by-products, and require extra steps to carry out the enantiomeric resolution.

The advantages of the process of this invention are:
1. cheap high yield chemical synthesis
   —CO to replace HCN
   —no non-recyclable by-products
   —very high conversions and selectivities
2. Diastereomers are created in the hydrocarboxylation step, eliminating the need for subsequent derivatization steps;
3. Easy product purification and by-product recycle.

In a particularly advantageous aspect of the invention we have 1provided a process which comprises (1) hydrocarboxylating an enol acylate with carbon monoxide and an organic hydroxyl compound having a chiral carbon atom, said organic hydroxyl compound being essentially only in either the L configuration or the D configuration, to produce a reaction mixture of diastereomeric α-acyloxy acid esters having two chiral centers, which mixture contains essentially no enantiomeric pairs, (2) separating the diastereomers by physical means, (3) hydrolyzing each diastereomer to make the L and D α-hydroxy acids, plus said organic hydroxyl compound, and (4) recycling at least a part of said hydroxyl compound to step (1).

European patent application no. 84 305611.0 published June 12, 1985, under Publication No. 0144118 discloses the details of how to hydrocarboxylate enol acylates with carbon monoxide and an organic hydroxyl compound. Reference is made to this document for the details of carrying out the hydrocarboxylation and the disclosures of this European patent application in this regard are incorporated herein by reference.

It should be noted that in such a hydrocarboxylation, the alpha carbon atom in the hydrocarboxylation product is chiral. Therefore, the α-acyloxy acid ester produced is a racemic mixture of the L and D forms. If one wants either the L form or the D form without its enantiomer, the separation is difficult and expensive.

The crux of the broadest aspect of the present invention is the concept of employing an organic hydroxyl compound starting material in the foregoing reaction that is essentially all L or all D so that when the reaction is carried out, the product will contain essentially no enantiomeric pairs, as previously discussed. Since the product mixture has no enantiomeric pairs, the stereoisomers can be more easily separated by physical means than can a reaction mixture containing enantiomeric pairs.

The hydrocarboxylation reaction is carried out catalytically, discussed in more detail hereafter. It can be carried out continuously or in a batch operation in the liquid or vapor phases. Usually the reaction is carried out in a batch operation in a solvent under pressure.

The reactant concentrations can vary widely and are not critical. The ratio of hydroxyl reactant to the enol ester is usually no greater than 10/1 on a molar basis and is preferably at least 1/1. The amount of carbon monoxide can vary widely, but it is preferred to carry out the reaction under a carbon monoxide pressure of 15 to 3500 psig, preferably 500 to 2500 psig. The amount catalyst can also vary widely. Most conveniently, the amount of catalyst is between 0.01 and 100 mole percent based on the enol ester, more usually 0.1 to 10 mole percent.

Usually, the reaction is carried out with a solvent. The solvent should be essentially inert under the reaction conditions and should dissolve the reactants and desirably the active catalyst species, although heterogeneous catalysts are possible. Suitable solvents are tetrahydrofuran, benzene, $CH_3CN$, diethyl ether, diethylene glycol dimethyl ether, $CH_2Cl_2$ and $CH_3Cl$. The now preferred solvent is tetrahydrofuran, particularly when using $(\phi_3P)_2PdCl_2$ or $Pd(P\phi_3)_4$ catalyst, or other palladium compounds, although an excess of the hydroxyl compound is also especially useful. Usually, the amount of solvent in the system will be such that the enol ester concentration is at least about 0.01 weight percent in the solution. A special case of a solvent that is not inert, strictly speaking, under the reaction conditions is either of the starting material reactants, i.e., the enol ester or the hydroxy compound. Either can be used in excess of the stoichiometric amount to react with the other reactant. Use of a large excess of the organic hydroxyl compound whether or not another solvent, such as THF, is present, helps produce appreciable amounts of the α-hydroxy acid ester; thus, the Acyl group is transesterified during the main carboxylation step.

The reaction is normally carried out at a temperature of 0° to 250° C., preferably 20° to 150° C. However, the reaction temperature can be below or above this if desired. As will be understood, optimum reaction temperature varies with the specific reactants. Reaction times on the order of 0.1 to 250 hours can be employed, with reaction times on the order of 2 to 50 hours being more convenient.

Catalysts useful are generally transition metal compounds, particularly coordination complexes of such metals. Palladium coordination complexes are remarkably effective, and especially those complexed with a phosphine, such as $P\phi_3$. Especially useful Pd complexes are $(\phi_3P)_2PdCl_2$ and $(\phi_3P)_4Pd$ with or without a promoter or "co-catalyst" such as HCl or $P\phi_3$.

Other useful catalysts include complexes of Co, Rh, Ni, and other transition metals. When Co complexes are used it is advantageous to incorporate hydrogen and a tertiary amine, pyridine or a pyridine derivative into the reaction mixture to enhance catalytic activity.

Once the hydrocarboxylation reaction is completed, the product α-acyloxy acid ester diastereomers can be recovered from the reaction system in a conventional manner, such as for example, by vacuum distillation or crystallization.

The product mixtures made by the process of the invention are useful, of course, to make the essentially pure L-α-hydroxy acids and D-α-hydroxy acids. In addition to the many recognized uses for these products, such as lactic acid and hydroxy acetic acid, all of the enantiomerically pure α-hydroxy acids that can be made from the diastereomeric ester mixtures produced by the process of the invention are useful in chiral gas or liquid chromatographic columns. Thus, the solid adsorbent of a chromatographic column that has pendant OH or —COOH groups can be esterified with the L or D alpha hydroxy acid or the α-acyloxy acid ester (usually the former) to make a chiral column.

Each of the α-hydroxy acids can also be used as a standard reference liquid to calibrate an instrument for measuring optical rotation of asymmetric compounds.

The α-hydroxy acids and the α-acyloxy acid esters made according to the present process can also be used to prepare specific gravity fluids of different specific gravities in order to determine the density of a solid by the sink or float method.

The following examples are illustrative only and are not to be considered in any way limiting.

EXAMPLE 1

A 70 mL stainless steel high pressure reactor fitted with a Pyrex glass liner and magnetic stir bar is charged with THF (5 mL), $(PPh_3)_2PdCl_2$ (0.05 mmol), L-menthoxyethanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-lactate and L-menthoxyethyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-menthoxyethanol, which is thereafter recycled to a repeat of the foregoing hydrocarboxylation reaction.

EXAMPLE 2

A 70 mL stainless steel high pressure reactor fitted with a Pyrex glass liner and magnetic stir bar is charged with THF (5 mL), $(PPh_3)_2PdCl_2$ (0.05 mmol), L-menthol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthyl acetyl-L-lactate and L-menthyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-menthol, which is thereafter recycled to a repeat of the foregoing hydrocarboxylation reaction.

EXAMPLE 3

A 70 mL stainless steel high pressure reactor fitted with a Pyrex glass liner and magnetic stir bar is charged with THF (5 mL), $(PPh_3)_2PdCl_2$ (0.05 mmol), L-2-butanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-2-butyl acetyl-L-lactate and L-2-butyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-2-butanol, which is thereafter recycled to a repeat of the foregoing hydrocarboxylation reaction.

EXAMPLE 4

A 70 mL stainless steel high pressure reactor fitted with a Pyrex glass liner and magnetic stir bar is charged with THF (5 mL), $(PPh_3)_2PdCl_2$ (0.05 mmol), D-2-butanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of D-2-butyl acetyl-L-lactate and D-2-butyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and D-2-butanol, which is thereafter recycled to a repeat of the foregoing hydrocarboxylation reaction.

EXAMPLE 5

A 70 mL steel high pressure reactor fitted with a Pyrex glass liner and magnetic stir bar is charged with THF (5 mL), $(PPh_3)_2PdCl_2$ (0.05 mmol), L-2-octanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-2-octyl acetyl-L-lactate and L-2-octyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-2-octanol, which is thereafter recycled to a repeat of the foregoing hydrocarboxylation reaction.

EXAMPLE 6

A 70 mL stainless steel high pressure reactor fitted with a Pyrex glass liner and magnetic stir bar is charged with THF (5 mL), $(PPh_3)_2PdCl_2$ (0.05 mmol), D-2-octanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of D-2-octyl acetyl-L-lactate and D-2-octyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and D-2-octanol, which is thereafter recycled to a repeat of the foregoing hydrocarboxylation reaction.

EXAMPLE 7

A 70 mL stainless steel high pressure reactor fitted with a Pyrex glass liner and magnetic stir bar is charged with THF (5 mL), $(PPh_3)_2PdCl_2$ (0.05 mmol), L-3-methoxy-1-butanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-3-methoxy-1-butyl acetyl-L-lactate and L-3-methoxy-1-butyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-3-methoxy-1-butanol, which is thereafter recycled to a repeat of the foregoing hydrocarboxylation reaction.

EXAMPLE 8

A 70 mL stainless steel high pressure reactor fitted with a Pyrex glass liner and magnetic stir bar is charged with THF (5 mL), $(PPh_3)_2PdCl_2$ (0.05 mmol), D-3-methoxy-1-butanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of D-3-methoxy-1-butyl acetyl-L-lactate and D-3-methoxy-1-butyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and D-3-methoxy-1-butanol, which is thereafter recycled to a repeat of the foregoing hydrocarboxylation reaction.

EXAMPLE 9

A 70 mL stainless steel high pressure reactor fitted with a Pyrex glass liner and magnetic stir bar is charged with THF (5 mL), $(Ph_3P)_4Pd$ (0.05 mmol), HCl (0.1 mmol), L-menthoxyethanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-lactate and L-menthoxyethyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-menthoxyethanol, which is thereafter recycled to a repeat of the foregoing hydrocarboxylation reaction.

EXAMPLE 10

A 70 mL stainless steel high pressure reactor fitted with a Pyrex glass liner and magnetic stir bar is charged with THF (5 mL), $RhCl_3\ H_2O$ (0.05 mmol), HI (0.1 mmol), L-menthoxyethanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-lactate and L-menthoxyethyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-menthoxyethanol, which is thereafter recycled to a repeat of the foregoing hydrocarboxylation reaction.

EXAMPLE 11

A 70 mL stainless steel high pressure reactor fitted with a Pyrex glass liner and magnetic stir bar is charged with THF (5 mL), $NiI_2\ 6H_2O$ (0.05 mmol), L-menthoxyethanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-lactate and L-menthoxyethyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-menthoxyethanol, which is thereafter recycled to a repeat of the foregoing hydrocarboxylation reaction.

EXAMPLE 12

A 70 mL stainless steel high pressure reactor fitted with a Pyrex glass liner and magnetic stir bar is charged with THF (5 mL), $Ph_3P)hd\ 2Ni(CO)_2$ (0.05 mmol), L-menthoxyethanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-lactate and L-menthoxyethyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-menthoxyethanol, which is thereafter recycled to a repeat of the foregoing hydrocarboxylation reaction.

EXAMPLE 13

A 70 mL stainless steel high pressure reactor fitted with a Pyrex glass liner and magnetic stir bar is charged with THF (5 mL), $[Rh(CO)_2Cl]_2$ (0.05 mmol), L-menthoxyethanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-lactate and L-menthoxyethyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-menthoxyethanol, which is thereafter recycled to a repeat of the foregoing hydrocarboxylation reaction.

EXAMPLE 14

A 70 mL stainless steel high pressure reactor fitted with a Pyrex glass liner and magnetic stir bar is charged with THF (5 mL), palladium acetate (0.05 mmol), L-menthoxyethanol (0.5 mmol), and vinyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-lactate and L-menthoxyethyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-menthoxyethanol, which is thereafter recycled to a repeat of the foregoing hydrocarboxylation reaction.

EXAMPLE 15

A 70 mL stainless steel high pressure reactor fitted with a Pyrex glass liner and magnetic stir bar is charged with THF (5 mL), $Co_2(CO)_8$ (0.05 mmol), pyridine (0.50 mmol), L-menthoxyethanol (0.5 mmol), and vinyl acetate (0.5 mmol). The reactor is sealed, pressurized to 1500 psig with 3:1 $CO:H_2$, and stirred for 24 hours at 100° C. The product mixture, isolated after removal of gas from the reactor vessel, contains a diastereomeric mixture of L-menthoxyethyl acetyl-L-lactate and L-menthoxyethyl acetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, acetic acid, and L-menthoxyethanol, which is thereafter recycled to a repeat of the foregoing hydrocarboxylation reaction.

EXAMPLE 16

A 70 mL stainless steel high pressure reactor fitted with a Pyrex glass liner and magnetic stir bar is charged with THF (5 mL), $(PPh_3)_2PdCl_2$ (0.05 mmol), L-menthoxyethanol (0.5 mmol), and vinyl propionate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl propionyl-L-lactate and L-menthoxyethyl propionyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, propionic acid, and L-menthoxyethanol, which is thereafter recycled to a repeat of the foregoing hydrocarboxylation reaction.

EXAMPLE 17

A 70 mL stainless steel high pressure reactor fitted with a Pyrex glass liner and magnetic stir bar is charged with THF (5 mL), (PPh$_3$)$_2$PdCl$_2$ (0.05 mmol), L-menthoxyethanol (0.5 mmol), and vinyl valerate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl valeryl-L-lactate and L-menthoxyethyl valeryl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, valeric acid, and L-menthoxyethanol, which is thereafter recycled to a repeat of the foregoing hydrocarboxylation reaction.

EXAMPLE 18

A 70 mL stainless steel high pressure reactor fitted with a Pyrex glass liner and magnetic stir bar is charged with THF (5 mL), (PPh$_3$)$_2$PdCl$_2$ (0.05 mmol), L-menthoxyethanol (0.5 mmol), and vinyl benzoate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl benzoyl-L-lactate and L-menthoxyethyl benzoyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, benzoic acid, and L-menthoxyethanol, which is thereafter recycled to a repeat of the foregoing hydrocarboxylation reaction.

EXAMPLE 19

A 70 mL stainless steel high pressure reactor fitted with a Pyrex glass liner and magnetic stir bar is charged with THF (5 mL), (PPh$_3$)$_2$PdCl$_2$ (0.05 mmol), L-menthoxyethanol (0.5 mmol), and 1-propenyl acetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-2-hydroxybutyrate and L-menthoxyethyl acetyl-D-2-hydroxybutyrate. The diastereomers are separated by preparative gas chromatography using an SE-30 liquid phase column. Each diastereomer is hydrolyzed separately by treatment with 2N HCl (aq) for 2 hours at 100° C. to give pure L- and D-2-hydroxybutyric acid, acetic acid, and L-menthoxyethanol, which is thereafter recycled to a repeat of the foregoing hydrocarboxylation reaction.

EXAMPLE 20

A 70 mL stainless steel high pressure reactor fitted with a Pyrex glass liner and magnetic stir bar is charged with THF (5 mL), (PPH$_3$)$_2$PdCl$_2$ (0.05 mmol), L-menthoxyethanol (0.5 mmol), and 2-acetyloxy-2-butene (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-2-methyl-2-hydroxybutyrate and L-menthoxyethyl acetyl-D-2-methyl-2-hydroxybutyrate. The diastereomers are separated by preparative gas chromatography using an SE-30 liquid phase column. Each diastereomer is hydrolyzed separately by treatment with 2N HCl (aq) for 2 hours at 100° C. to give pure L- and D-2-methyl-2-hydroxybutyric acid, acetic acid, and L-menthoxyethanol, which is thereafter recycled to a repeat of the foregoing hydrocarboxylation reaction.

EXAMPLE 21

A 70 mL stainless steel high pressure reactor fitted with a Pyrex glass liner and magnetic stir bar is charged with THF (5 mL), (PPh$_3$)$_2$PdCl$_2$ (0.05 mmol), L-menthoxyethanol (0.5 mmol), and 1-acetyloxy-2-methylpropene (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-3-methyl-2-hydroxybutyrate and L-menthoxyethyl acetyl-D-3-methyl-2-hydroxybutyrate. The diastereomers are separated by preparative gas chromatography using an SE-30 liquid phase column. Each diastereomer is hydrolyzed separately by treatment by 2N HCl (aq) for 2 hours at 100° C. to give pure L- and D-3-methyl-2-hydroxybutyric acid, acetic acid, and L-menthoxyethanol, which is thereafter recycled to a repeat of the foregoing hydrocarboxylation reaction.

EXAMPLE 22

A 70 mL stainless steel high pressure reactor fitted with a Pyrex glass liner and magnetic stir bar is charged with THF (5 mL), (PPh$_3$)$_2$PdCl$_2$ (0.05 mmol), L-menthoxyethanol (0.5 mmol), and 2-acetyloxy-3-methyl-2-butene (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-2-hydroxy-2,3-dimethylbutyrate and L-menthoxyethyl acetyl-D-2-hydroxy-2,3-dimethylbutyrate. The diastereomers are separated by preparative gas chromatography using an SE-30 liquid phase column. Each diastereomer is hydrolyzed separately by treatment with 2N HCl (aq) for 2 hours at 100° C. to give pure L- and D-2-hydroxy-2,3-dimethylbutyric acid, acetic acid and L-menthoxyethanol, which is thereafter recycled to a repeat of the foregoing hydrocarboxylation reaction.

EXAMPLE 23

A 70 mL stainless steel high pressure reactor fitted with a Pyrex glass liner and magnetic stir bar is charged with THF (5 mL), (PPh$_3$)$_2$PdCl$_2$ (0.05 mmol), L-menthoxyethanol (0.5 mmol), and 1-acetyloxy-3-methylthiopropene (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyethyl acetyl-L-2-hydroxy-4-methylthiobutyrate and L-menthoxyethyl acetyl-D-2-hydroxy-4-methylthiobutyrate. The diastereomers are separated by preparative gas chromatography using an SE-30 liquid phase column. Each diastereomer is hydrolyzed separately by treatment with 2N HCl (aq) for 2 hours at 100° C. to give pure L- and D-2-hydroxy-4-methylthiobutyric acid (methionine hydroxy analog), acetic acid, and L-menthoxyethanol, which is thereafter recycled to a repeat of the foregoing hydrocarboxylation reaction.

As used herein the term "hydroxyl" in the phrase "organic hydroxyl compound" excludes the hydroxyl group of a carboxylic acid group, —COOH.

As will be evident to those skilled in the art, various modifications of this invention can be made or followed in the light of the foregoing disclosure and discussion without departing from the spirit and scope of the disclosure or from the scope of the claims.

We claim:

1. In the process of hydrocarboxylating an enol acylate with CO and an organic hydroxyl compound to produce an α-acyloxy acid ester whose alpha C atom is chiral, the improvement comprising using as the organic hydroxyl compound reactant, an organic hydroxyl compound which also has a chiral center that is essentially all L or D, thereby producing a reaction mixture having essentially no enantiomeric pairs and containing diastereomeric α-acyloxy acid esters having two chiral centers, said hydrocarboxylating simultaneously creating (1) said ester, (2) the chirality of said alpha C atom in L, D form and and (3) the second chiral center in said ester in essentially all L or all D form.

2. A process which comprises (1) hydrocarboxylating an enol acylate with carbon monoxide and organic hydroxyl compound having a chiral carbon atom, said organic hydroxyl compound being essentially only in either the L configuration or the D configuration, to produce a reaction mixture of diastereomeric α-acyloxy acid esters having two chiral centers, which mixture contains essentially no enantiomeric pairs (2) separating the diastereomers by physical means, (3) hydrolyzing each diastereomer to make the L and D α-hydroxy acids plus said L or D organic hydroxyl compound, and (4) recycling at least a part of said organic hydroxyl compound to step (1), said hydrocarboxylating simultaneously creating (a) said ester, (b) the chirality of said alpha C atom in L, D form and (c) the second chiral center in said ester in essentially all L or all D form.

* * * * *